United States Patent
Stürmer

(10) Patent No.: US 7,259,264 B2
(45) Date of Patent: Aug. 21, 2007

(54) 3-METHYLAMINO-1-(2-THIENYL)-1-PROPANONE, PRODUCTION AND USE THEREOF

(75) Inventor: Rainer Stürmer, Rödersheim-Gronau (DE)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 10/542,003

(22) PCT Filed: Jan. 15, 2004

(86) PCT No.: PCT/EP2004/000237

§ 371 (c)(1),
(2), (4) Date: Jul. 12, 2005

(87) PCT Pub. No.: WO2004/065376

PCT Pub. Date: Aug. 5, 2004

(65) Prior Publication Data

US 2006/0128791 A1    Jun. 15, 2006

(30) Foreign Application Priority Data

Jan. 22, 2003    (DE) ................. 103 02 595

(51) Int. Cl.
*C07D 333/16*    (2006.01)
*C07D 333/20*    (2006.01)

(52) U.S. Cl. ........................... 549/72; 549/74

(58) Field of Classification Search ............... 549/72, 549/74
See application file for complete search history.

(56) References Cited

U.S. PATENT DOCUMENTS

2005/0261514 A1* 11/2005 Kralik et al. ............... 560/170

FOREIGN PATENT DOCUMENTS

| EP | 0 273 658 | 7/1988 |
| EP | 0 457 559 | 11/1991 |
| EP | 0 650 965 | 5/1995 |
| WO | WO-2004/005239 A1 | 1/2004 |
| WO | WO-2004/020391 | 3/2004 |

OTHER PUBLICATIONS

El-Khawaga, A. M. et al., "Modern Friedel-Crafts chemistry XVI. Reaction of Thiophene With Bifunctional Molecules Under Different Friedel-Crafts Catalysts: Attempted Synthesis of Cyclopenta(b) Thiophenes and Dihydrobenzo(b) Thiophenes," Phosphorus and Sulfur 33 (1987), pp. 25-31.

Deeter, J. et al., "Asymmetric Synthesis And Absolute Stereochemistry of LY248686", Tetrahedron Letters, 31 (49) (1990), pp. 7101-7104.

Liu, H. et al., "Chemo-Enzymatic Synthesis Of The Antidepressant Duloxetine And Its Enantiomer", Chirality 12 (2000) pp. 26-29.

Sorbera, L. A. et al., "Duloxetine Oxalata, Treatment of Stress Urinary Incontinence, Antidepressant, Norepinephrine Reuptake Inhibitor, 5-HT Reuptake Inhibitor", Drugs of the Future 25 (9) (2000), pp. 907-916.

Wheeler, W. J. et al., "An Asymmetric Synthesis Of Duloxetine Hydrochloride, A Mixed Uptake Inhibitor Of Serotonin And Norepinephrine, And Its C-14 Labeled Isotopomers", Journal of Labelled Compounds and Radiopharmaceuticals, 36 (3) (1995), pp. 213-223.

* cited by examiner

*Primary Examiner*—Rebecca Anderson
*Assistant Examiner*—Karen Cheng
(74) *Attorney, Agent, or Firm*—Connolly Bove Lodge & Hutz LLP

(57) ABSTRACT

The present invention relates to the preparation of 3-methylamino-1-(2-thienyl)-1-propanone and its use for preparing the pharmaceutical (+)-(S)-N-methyl-3-(1-naphthyloxy)-3-(2-thienyl)propylamine oxalate—(trade name Duloxetine®).

1 Claim, 1 Drawing Sheet

3-METHYLAMINO-1-(2-THIE NYL)-1-PROPANONE, PRODUCTION AND USE THEREOF

RELATED APPLICATIONS

Figure 1:
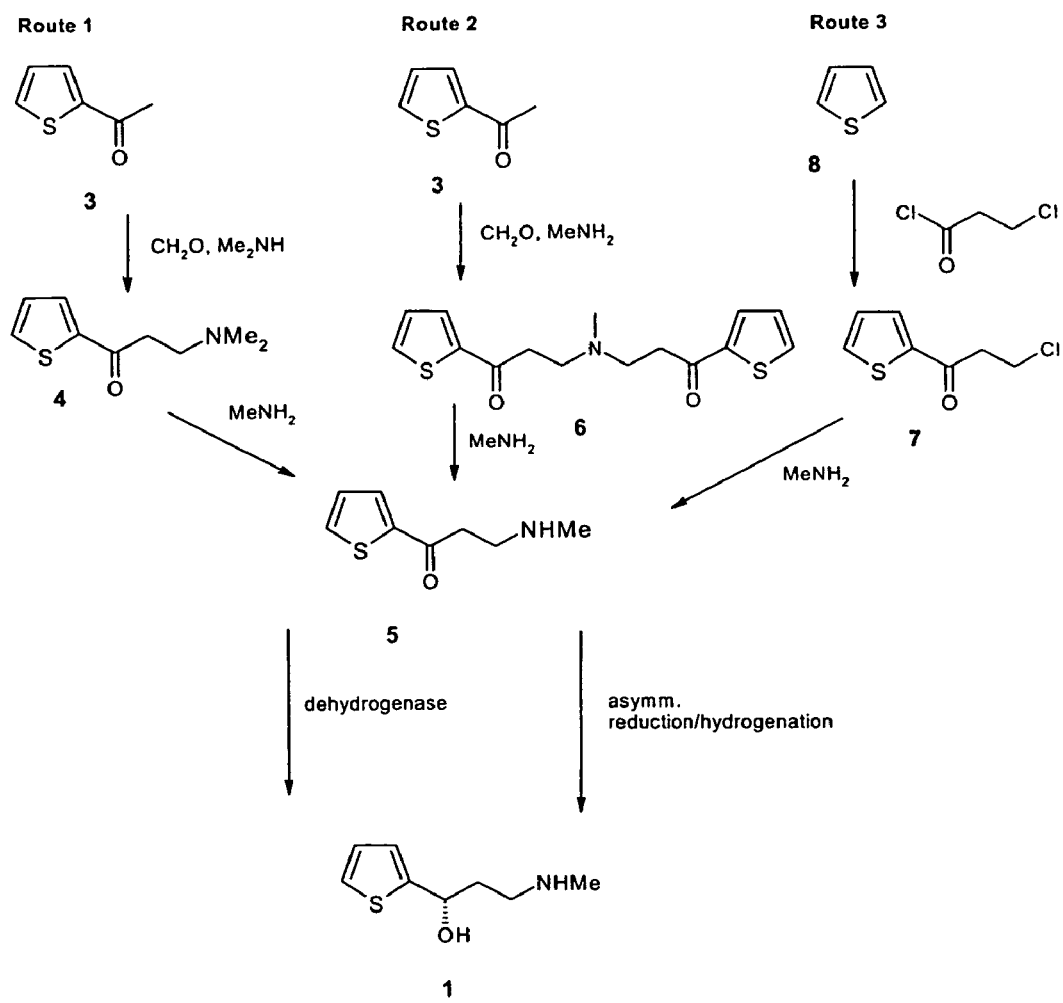

This application is a national stage application (under 35 U.S.C. 371) of PCT/EP2004/000237 filed Jan. 15, 2004 which claims benefit to German application 103 02 595.2 filed Jan. 22, 2003.

The present invention relates to the preparation and use of 3-methylamino-1-(2-thienyl)-1-propanone.

The amino alcohol 1 (FIG. 1) [(1S)-3-methylamino-1-(2-thienyl)propan-1-ol] is a sought-after intermediate in the preparation of a pharmaceutical ((+)-(S)-N-methyl-3-(1-naphthyloxy)-3-(2-thienyl)propylamine oxalate—trade name Duloxetine®). The method which has been used thus far for preparing this intermediate is elaborate and requires expensive and labile reagents. Furthermore, a technically elaborate chromatography is required for preparing a pure compound. See, for example, EP 273658 A1; Liu et.al., Chirality 2000, 12 (1), 26-29; Wheeler et. al, J. Labelled Comp. Radiopharm. 1995, 36(3), 213-23; U.S. Pat. No. 5,362,886, EP 457559, Deeter et al , Tet. Lett. 1990, 31(49), 7101-4; EP 0650965; L. A. Sorbera, R. M. Castaner, J. Castaner, Drugs of the Future 2000, 25(9): 907-916.

The object therefore was to make available simpler and more economical processes for preparing Duloxetine®.

The present invention describes novel and economical processes for obtaining the isomerically pure compound 1. As an intermediate which they share in common, the processes according to the invention use the novel ketone 5 (FIG. 1) [3-methylamino-1-(2-thienyl)-1-propanone], from which the amino alcohol 1 can be obtained by means of enantioselective reduction. The subsequent reaction of the aminoalcohol 1 to give Duloxetine® is well known to the skilled person and can be carried out in analogy with the process described in EP 0457559 A2 (reaction with 1-fluoronaphthalene).

The invention relates to 3-methylamino-1-(2-thienyl)-1-propanone (FIG. 1, compound 5) and its acid addition salts. The acid addition salts of compound 5 are products of the reaction of compound 5 with inorganic or organic acids. Acids which are particularly suitable for this purpose are hydrochloric acid, sulfuric acid, phosphoric acid, oxalic acid, fumaric acid, maleic acid and acetic acid.

The starting compound for preparing the ketone 5 or the amino alcohol 1 can be thiophene or 2-acetylthiophene. FIG. 1 depicts three routes for preparing the ketone 5 (routes 1 to 3), which routes are described below:

Route 1

Compound 4 is obtained by way of a classical Mannich reaction starting with acetylthiophene, formaldehyde and dimethylamine (EP 0457559 A2 Example 1). The monomethylamino ketone 5 is obtained by means of a retromichael/Michael reaction, by reacting 4 with an excess of methylamine.

Route 2

Compound 6 is obtained by means of a classical Mannich reaction starting with acetylthiophene, formaldehyde and methylamine (Blicke; Burckhalter; JACSAT; J. Amer. Chem. Soc.; 64; 1942; 451, 453). The monomethylamino ketone 5 is obtained by means of a retromichael/Michael reaction, by reacting 6 with an excess of methylamine.

Route 3

The compound 7 is obtained by means of a classical Friedel-crafts acylation of thiophene 8 with 3-chloropropionyl chloride (described in El-Khagawa, Ahmed M.; El-Zohry, Maher F.; Ismail, Mohamed T.; PREEDF; Phosphorus Sulfur; EN; 33; 1987; 25-32). The monomethylamino ketone 5 is obtained by reaction with methylamine.

The invention also relates to the use of 3-methylamino-1-(2-thienyl)-1-propanone or its acid addition salts for preparing N-methyl-3-(1-naphthyloxy)-3-(2-thienyl)propylamine, or its acid addition salts, in racemic or enantiomerically pure form. Particular preference is given to the use for preparing (+)-(S)-N-methyl-3-(1-naphthyloxy)-3-(2-thienyl)propylamine oxalate (Duloxetin®).

The invention also relates to a process for preparing N-methyl-3-(1-naphthyloxy)-3-(2-thienyl)propylamine, or its acid addition salts, in racemic form or, preferably, in enantiomerically pure form, with 3-methylamino-1-(2-thienyl)-1-propanone or its acid addition salts being prepared as intermediate in a first step with this intermediate then being reduced to the corresponding alcohol.

The reduction can be carried out either under racemizing conditions or enantioselectively. Preference is given to an enantioselective reduction, in particular to such a reduction which yields the (S)-enantiomer 1 as the product.

This can be carried out either chemically, using classical enantioselective hydrogenation methods,. such as using $NaBH_4$ or $LiAlH_4$, which are provided with chiral ligands for the purpose of achieving enantioselectivity, or using transition metal-containing hydrogenation catalysts or using enzymic reductions, for example using microbial, in particular bacterial or fungal, dehydrogenases.

Experimental:

Route 1:

5 g of dimethylamino ketone 4 are initially introduced as the hydrochloride in 25 ml of ethanol after which 20 eq. of methylamine (40% in water) are added dropwise and the mixture is stirred at 60-70° C. for 6 h. After the reaction has come to an end, part of the ethanol is removed and the product 5 is obtained as a white crystalline solid (yield, 3.45 g as the hydrochloride).

Route 2:

5 g of diketone 6 are initially introduced, as the hydrochloride, in 25 ml of ethanol after which 20 eq. of methylamine (40% in water) are added dropwise and the mixture is stirred at 70-80° C. for 6 h. After the reaction has come to an end, part of the ethanol is removed and the product 5 is obtained as a white crystalline solid (yield, 3.87 g as the hydrochloride).

Route 3:

5 g of chloroketone 7 are initially introduced in 25 ml of THF after which 20 eq. of methylamine (40% in water) are added dropwise and the mixture is stirred at 30-40° C. for 6 h. After the reaction has come to an end, most of the THF is removed and the product 5 is isolated as a white crystalline solid (yield, 4.10 g as the hydrochloride).

In routes 1-3, aqueous methylamine can also be replaced with gaseous or liquefied methylamine.

Spectroscopic data for the monomethylamino ketone 5 as the hydrochloride:

$^{13}$C NMR (D$_2$O, 125 MHz) spin-echo multiplicities in brackets: δ (ppm)=188.5 (s), 140.4 (s), 139.2 (d), 137.8 (d), 131.9 (d), 46.9 (t), 37.3 (t), 36.0 (q) $^1$H NMR (D$_2$O, 500MHz): δ (ppm)=8.00 (m, 1H), 7.95 (m, 1H), 7.25 (m, 1H), 3.40 (m,2H), 2.75 (m, 2H), 2.62 (s, 3H)

Reduction of compound 5 to give compound 1 (FIG. 1) NaBH4 (racemic):

5 g of methylamino ketone 5 were initially introduced in 20 ml of ethanol after which 0.8 eq. of NaBH4 was added in portions at 20° C. After the mixture had been stirred for 6 h, it was subjected to aqueous workup. The racemic monomethylaminoalcohol 1 was obtained as a pale yellow solid (yield: 3.9 g)

1H NMR (500 MHz, CDCl3) δ(ppm)=2.1 (m, 2H), 2.5 (s, 3H), 2.9 (m, 2H), 4.5 (br s, 2H), 5.25 (m, 1H), 6.94 (m, 1H), 7.00 (m, 1H), 7.22 (m,1H) 13C NMR (125 MHz, CDCl3) δ (ppm)=35.4, 36.3, 49.7, 71.4, 122.5, 123.8, 126.6, 149.3

LiAlH4 (chirally modified) carried out as in EP 0457559 A2, example 1B (enantioselectively).

The yield of 1 was 74%, with an enantiomeric purity of 72% ee.

I claim:

1. A process for preparing (+)-(S)-N-methyl-3-(l-naphthyloxy)-3-(2-thienyl)propylamine oxalate, wherein 3-methylamino-1-(2-thienyl)-1-propanone, or an acid addition salt thereof, is prepared as intermediate by reacting thiophene with 3-Chloropropionic acid chloride and subsequent reaction with methylamine wherein the 3-methylamino-1-(2-thienyl)-1-propanone, or an acid addition salt thereof, is reduced to (1S)-3-methylamino-1-(2-thienyl)propan-1-ol, or an acid addition salt thereof and the reduction is carried out using a microbial dehydrogenase.

* * * * *

UNITED STATES PATENT AND TRADEMARK OFFICE
CERTIFICATE OF CORRECTION

| | | |
|---|---|---|
| PATENT NO. | : 7,259,264 B2 | Page 1 of 1 |
| APPLICATION NO. | : 10/542003 | |
| DATED | : August 21, 2007 | |
| INVENTOR(S) | : Rainer Stürmer | |

It is certified that error appears in the above-identified patent and that said Letters Patent is hereby corrected as shown below:

On the Title Page: item (56),

In the References Cited, please insert under the heading U.S. patent documents --5,362,886 11/1994 Berglund 549/75 --.

Signed and Sealed this

Twenty-fourth Day of February, 2009

JOHN DOLL
*Acting Director of the United States Patent and Trademark Office*